(12) United States Patent
Baugh

(10) Patent No.: US 6,184,791 B1
(45) Date of Patent: Feb. 6, 2001

(54) VEHICLE SAFETY WARNING AND ACTION SYSTEM

(76) Inventor: Gerald R. Baugh, 12444 NW. Kearney St., Portland, OR (US) 97229

( * ) Notice: Under 35 U.S.C. 154(b), the term of this patent shall be extended for 0 days.

(21) Appl. No.: 09/492,424

(22) Filed: Jan. 27, 2000

(51) Int. Cl.[7] .................................................. G08B 23/00
(52) U.S. Cl. .......................... 340/576; 340/575; 340/439; 128/782
(58) Field of Search ............................ 340/576, 575, 340/573.1, 439; 128/782, 272, 644, 733, 774

(56) References Cited

U.S. PATENT DOCUMENTS

| | | |
|---|---|---|
| 3,999,177 | 12/1976 | Greene . |
| 4,272,764 | 6/1981 | Herr et al. . |
| 4,836,219 * | 6/1989 | Hobson et al. ........................ 350/575 |
| 5,353,013 | 10/1994 | Estrada . |
| 5,522,092 | 6/1996 | Streb et al. . |
| 5,581,239 * | 12/1996 | Lin ......................................... 340/575 |
| 5,684,461 | 11/1997 | Jones . |
| 5,691,693 | 11/1997 | Kithil . |
| 5,907,282 * | 5/1999 | Tuorto et al. ......................... 340/576 |
| 6,049,747 * | 4/2000 | Nakajima et al. ..................... 701/45 |
| 6,057,768 * | 5/2000 | Barnoach ............................. 340/575 |
| 6,067,020 * | 5/2000 | Wimmer ............................... 340/575 |
| 6,087,941 * | 7/2000 | Ferraz .................................. 340/575 |

\* cited by examiner

Primary Examiner—Nina Tong
(74) Attorney, Agent, or Firm—Kolisch Hartwell Dickinson McCormack & Heuser

(57) ABSTRACT

A multi-stage vehicle safety warning and action system which monitors a driver's head position as an indication about whether that driver is nominally in proper control of the vehicle. The system features a laser-beam source which is worn on a driver's head and which is generally aimed toward a system light-sensitive structure. The point of impingement of the beam from the source relative to the light-sensitive structure determines the need of the system to give a warning or to take some other form of safety action. Timing is used by the system to differentiate normal driver head movement from abnormal movement.

10 Claims, 1 Drawing Sheet

VEHICLE SAFETY WARNING AND ACTION SYSTEM

BACKGROUND AND SUMMARY OF THE INVENTION

This invention pertains to a safety warning and action system intended for use in a vehicle, such as an automobile or a truck, to produce both internal and external warnings, and, if need be, certain additional kinds of safety actions, under circumstances where it appears that the driver, for whatever reason, is no longer in control of the vehicle. More specifically, it relates to such a system that effectively monitors the position and orientation of a driver's head, and which, in preferably three, appropriate, timed stages that generally relate to three potentially, progressively dangerous emergency states, produces related warnings and generates related safety actions when that head position and orientation seem to be abnormal (non-attentive to proper driving).

According to a preferred embodiment of the instant invented system, which system is also referred to herein as a multistage emergency response and action system, a vehicle driver is provided with, and wears, something like a head band (headgear) on which there is suitably mounted an electrically-powered light source, such as a laser beam source. A photosensitive, light-beam monitoring (or sensing) structure which also forms part of the system is disposed within the vehicle, for example, on the inside of the windshield in front of the driver. So long as the beam from the source strikes inside the boundary of a defined non-emergency monitoring zone in the light-beam monitoring structure, driver behavior is deemed to be normal. However, and according to designed operation of the system of this invention, if the beam of light from the light source falls for a first predetermined time period outside the mentioned monitoring zone boundary, resulting, for example, because the driver's head nods forwardly or rearwardly, or to one side or the other, a selected pattern (preferably time dependent) of warnings and/or other actions begins to take place under the control of the invented system.

The preferred embodiment of the invention, as was just stated, features a system wherein the light-beam monitoring structure is indeed carried on the inside of the windshield directly in front of the driver. However, variations are, of course, possible, and the proposed monitoring system could be located in other areas, such as overhead the driver, behind the driver's head, or in some other place.

In the specific mode of operation which characterizes the mentioned preferred embodiment, when the system detects that the beam from the light source has fallen outside of the designated non-emergency monitoring zone, and where this condition exists for a certain, and preferably selectable, first predetermined time interval, the system triggers first-stage action, and delivers to the driver an appropriate warning inside the vehicle.

Either simultaneous with that inside warning (and/or other inside-the-vehicle activity), or preferably slightly thereafter (second predetermined time interval), depending upon how timing activity within the system is set to occur, the system implements second-stage action, and initiates an external warning, such as a beeping horn or flashing lights or both, to announce to the outside world a probable driver problem.

If even thereafter, for a third predetermined time interval, a danger situation continues to exist, that third time interval being also dependent upon how timing behavior is set to occur in the system, the system initiates third-stage action, wherein it positively takes driving control, implementing, for example, the applying of brakes, and/or the decelerating and/or the turning off the engine, etc.

Communication between the source light beam and the mentioned monitoring structure is preferably confirmed in any suitable manner to avoid system response to some extraneous light source. Various conventional approaches, such as one featuring selectable pulsed encoding of the beam from the system light source, can be employed to accomplish system isolation from spurious, external light activity.

Several modifications of the system of the invention are also disclosed herein—modifications which relate to the construction and positioning of monitoring structure, as well as modifications which involve both the monitoring structure and the headgear worn by a driver. For example, one recognized modified form of the system employs headgear which carries photo-optical transceiver apparatus (a light source and a light-responsive receiver), and which employs optical retro-reflector material in the monitoring structure. Such monitoring structure, collectively with the mentioned head-gear, are referred to as optical driver-condition monitoring structure.

Several other modifications, and various other important features and advantages which are offered by the system of this invention will be disclosed hereinbelow, and will become more fully apparent in and as the detailed description which now follows is read in conjunction with the drawings.

DESCRIPTION OF THE DRAWINGS

FIG. 2 also serves to illustrate a modified form of system which includes a headgear-borne photo-optical transceiver structure, and a monitor structure which utilizes optical retro-reflector material.

DETAILED DESCRIPTION OF, AND BEST MODE FOR CARRYING OUT, THE INVENTION

Figure 1:
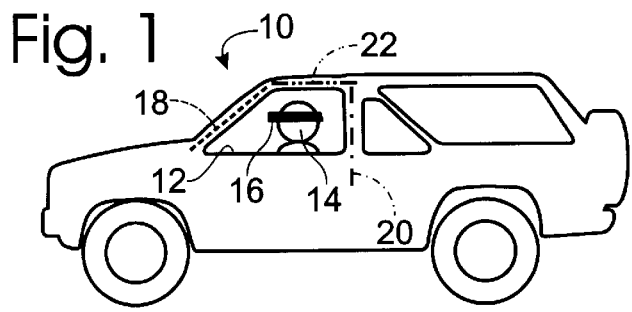
FIG. 1 is a simplified side elevation of an automotive SUV-type vehicle which is equipped with a preferred embodiment of the present invention.

Turning attention now to the drawings, and referring first of all to FIG. 1, here there is indicated generally at 10 an automotive vehicle, generally in the form of what is known as a sports utility vehicle (SUV), in which the preferred form of the system of the present invention has been suitably installed for use. Shown through the driver-side window 12 in this vehicle, and represented by a simple circle 14, is the head of a driver. The thick, horizontal darkened line, identified with the reference numeral 16 in FIG. 1, represents a head band, or headgear, which forms part of the system of this invention, and which is being worn on head 14. Suitably mounted on this head band is a battery-powered laser-beam device (not shown in this figure) which is intended to shine a thin beam of light forwardly toward the driver's side of the windshield. Specifically, it is constructed to aim a conventionally pulse-encoded light beam toward a forward photosensitive monitor, or light-beam sensing, structure 18 which is pictured schematically in dashed lines in FIG. 1. This monitor structure, which will be discussed more fully shortly, is suitably installed on the inside surface of the windshield in vehicle 10. The laser-beam device is also referred to herein both as light-beam active structure, and as a light-beam source.

Exact details of the constructions of head band 16, and of the mentioned laser light source, including such a source which is characterized by fixed or selectable pulse encodation, are not set forth herein inasmuch as they can each be built in a number of different conventional ways. The specific constructions of these components form no part of the present invention.

FIG. 1 also illustrates schematically two alternative (of many) operative locations wherein monitor structure 18 can be deployed. One of these is shown by a dash-dot line 20 in FIG. 1 directly behind the driver's head, and the other is shown by dash-double-dot line 22 directly over the driver's head. A bit more about these two, illustrated, alternative locations for the monitor structure will be mentioned later. Also to be mentioned later is a "view" of FIG. 1 which discloses a modified system wherein headgear 16 carries suitable photo-optical transceiver apparatus, and monitor structure 18 includes optical retro-reflector structure.

Figure 2:
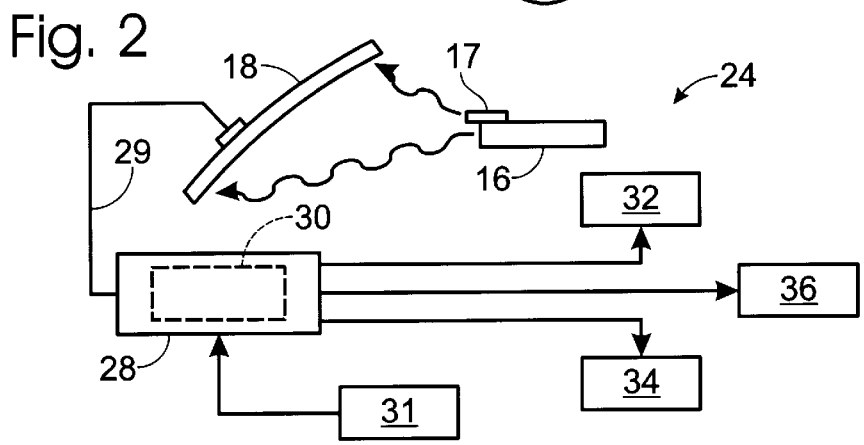
FIG. 2 is a block/schematic diagram which shows the system of FIG. 1 integrated with certain conventional, on-board vehicle system components that are present in the vehicle pictured in FIG. 1.
Figure 3:
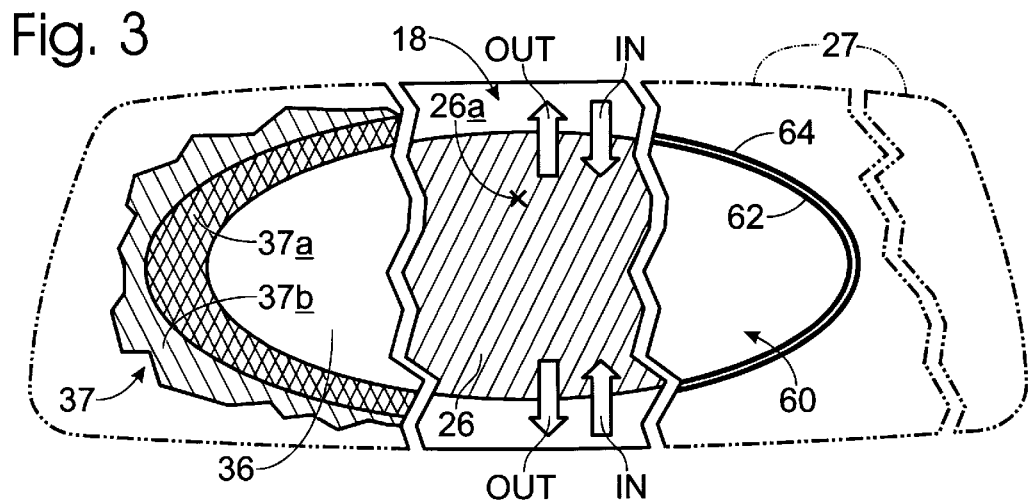
FIG. 3 is a schematic, fragmentary view which has been structured to illustrate (a) the preferred embodiment of a monitor structure that forms part of the present invention, and (b), additionally, several of many possible system modifications, including modifications of such monitor structure.

Looking now at FIGS. 2 and 3 (and first, specifically, the central portion of FIG. 3) along with FIG. 1, reference numeral 24 generally points to the preferred embodiment of the system of this invention. Head band 16 is here pictured as a horizontal rectangle which carries a forwardly projecting, pulse-encoded laser-beam source 17. In the condition of things generally pictured in FIG. 1, the pulsed/coded light beam from source 17 is generally aimed toward the windshield of the vehicle, and specifically toward previously-mentioned monitor structure 18.

While the specific laser-beam source now being discussed has been referred to earlier herein as being battery-powered, power for operating the source could as well be provided, via an appropriate conductive tether, directly from the vehicle's own electrical power system.

In the preferred embodiment of the invention which is now being described, monitor structure 18 preferably includes a single broad expanse of a suitable, substantially transparent photosensitive film that takes the form of a generally horizontally extending, elongate, somewhat ovate film, or panel, 26. Panel 26, shown only fragmentarily in FIG. 3, lies directly in front of the driver's head, is suitably applied to and mounted on the inside surface of the windshield in vehicle 10, and directly defines what is referred to herein as a non-emergency monitoring zone. Panel 26 can be formed of any suitable conventional transparent photosensitive material, such as the photovoltaic thin-film material known as Graetzel-cell material made by Silicon Technologies Australia Pty. Ltd. in Canberra, Australia.

In FIG. 3, panel 26 is seen to lie within the perimetral boundary of the windshield, which boundary is represented by a dash-double-dot line 27. All of the region inside vehicle 10 outside of the boundary of panel 26 constitutes an emergency monitoring zone.

According to the preferred embodiment of the invention, and as will be more fully explained shortly, staged warning and safety actions under the influence of system 24 will occur in preselected, time-separated stages when and if the beam from source 17 strikes, and remains for certain predetermined time intervals, anywhere in vehicle 10 outside the boundary of panel 26—i.e., outside of the above-mentioned non-emergency monitoring zone. More will be said below about this staged action.

Suitably operatively connected to film 26 in monitor structure 18, and also forming part of system 24, is monitor circuitry 28 (see FIG. 2) which includes an appropriate timer subcircuit shown by dashed block 30. Circuitry 28 is also referred to herein as response structure. Impingement of the light beam from source 17 on film 26 produces immediately a related output electrical signal on conductor structure 29 (FIG. 2), which signal is communicated to circuitry 28. This signal, which is preferably encoded in a suitable fashion to distinguish it from the actions of ambient, spurious light that strikes film 26, indicates a condition of appropriate, normal driving behavior.

When, however, the beam from source 17 disengages from film 26, a condition of non-normal driving behavior is indicated and the system of this invention prepares to act.

In particular, such a light-beam disengagement removes from circuitry 28 the electrical signal just above described, and initiates operation of the timer subcircuit, and thereafter effects an appropriate opening or closing of internal "switches" (not shown), electronic or mechanical, in circuitry 28, which "switches" activate, in predetermined stages (to be discussed more fully shortly), a pattern of warning and shutdown actions in the vehicle. Circuit construction (switching structure) in circuitry 28 which accomplishes this can take any one of a large number of different forms, all well-known to those skilled in the art. Accordingly, such specific circuit construction is not elaborated herein.

Continuing with what is shown in FIG. 2, appropriately also connected to circuitry 28 are (1) a power source 31, which preferably is the vehicle power source, (2) internal, audible warning structure 32 (such as a chime, a siren, etc.), (3) external audible and visual warning structure 34 (such as the horn, lights, etc.), and (4) safety action structure 36 (such as engine and brake control). These several connected structures are preferably ones that form part of vehicle 10.

Figure 4:
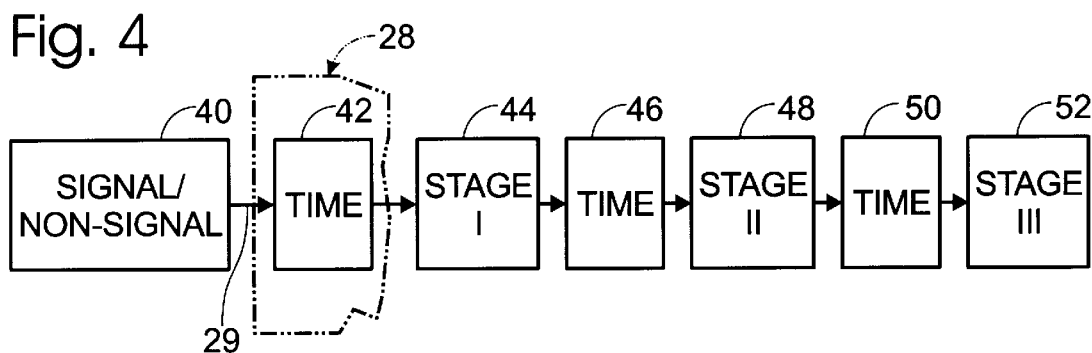
FIG. 4 is a simplified block diagram picturing the staged and timed flow of activities that occur during operation of the system of the invention when a driver emergency condition is detected.

A more detailed description now to be read along with FIG. 4, regarding how system 24 operates, will explain the cooperative workings of the various things pictured as rectangular blocks in FIG. 2.

Prior to placing system 24 into use, the using driver dons the headgear, turns on the system, and sits in the driver's seat with the laser beam aimed toward film 26 in monitor structure 18. Under these circumstances, the system is calibrated (in accordance with the particular driver using the system) by the driver facing the windshield, and causing, through appropriate adjustments made in the head band and in the laser source, the light beam from source 17 to strike a suitably marked spot, such as 26a (see FIG. 3), on film 26. The location, shape and size of film 26, and the position of spot 26a, are suitably arranged in such a fashion that normal, expected lateral turning, and raising and lowering, of the driver's head, after calibration, will result in the point of windshield impingement of the light beam being within the perimetral boundary of film 26.

Pictured at the upper and lower sides of film 26 centrally in FIG. 3 are two pairs of oppositely aimed arrows. These arrows (labeled "OUT" and "IN") symbolize reversible movements of the driver's head which causes movement of the beam impingement point first to the outside, and then later to the inside, of the perimetral boundary of film 26. If something occurs which causes the driver to lose focus on proper driving, for example by inadvertently turning, or raising or lowering, of the head in such a manner that the laser beam no longer strikes within film 26, or perhaps by the driver becoming suddenly ill or stricken with something such as a heart attack, the earlier-mentioned impingement-recognition electrical signal is removed from conductor structure 29, and is thus no longer furnished to circuitry 28. The signal/non-signal condition on conductor structure 29 is pictured schematically by block 40 in FIG. 4.

Following a selectable, predetermined, first-stage time interval after this condition comes into existence (which might just be a few seconds, or less than even a single second), system 24 initiates stage-one action. This first-stage time interval is implemented by timer-subcircuit 30, and is represented by a block 42 in FIG. 4. First-stage action is represented by a block 44 in FIG. 4.

Initially, and according to the preferred system embodiment now being discussed, the system effects the sounding of an appropriate internal audible warning, such as the sounding of a chime, siren, bell or something else, to alert the driver to take corrective action. Another preliminary action which might be taken is the turning on (with, for example, full-fan action) of the onboard vehicle air-conditioning system—an action which might just "wake up" the driver.

If a potential danger situation (i.e., no impingement of the light beam on film 26 ) lasts longer in time (second time interval) even after such a first-stage internal warning signal is given, the next thing which occurs is that system 24 begins a stage-two action. It does so preferably by implementing an external audible and/or visual warning, such as by the blowing of the horn, the flashing of headlights and taillights, etc., in order to alert drivers on the outside that vehicle 10 may not be under the proper control of its driver. This second time interval is determined by timer subcircuit 30, and is represented by a block 46 in FIG. 4. Stage-two action by system 24 is represented by a block 48 in FIG. 4.

If the condition of light-beam non-impingement on film 26 lasts even longer in time (third time interval), then circuitry 28 implements decisive third-stage safety action, taking control of the physical operation of vehicle 10 as, for example, by initiating the application of brakes, and/or by the shutting off of the engine. In FIG. 4, a block 50 represents determination by timer subcircuit 30 of elapse of this third time interval. A block 52 in FIG. 4 represents third-stage action by system 24.

In the operation of system 24 as so far described, if, within any of the three mentioned time intervals the driver's head returns to a normal position, then the specific action/warning stage which the system would otherwise have implemented had that time interval been "completed" will not take place. However, if a prior one of the warning/action stages has already been implemented and is currently "under way", it will not automatically be stopped. Such stopping will occur only under direct driver (or other-person) conscious action. This will help to assure that an emergency situation is in fact recognized, and under control.

In relation to the stopping of the activity of system 24 once warning or other safety activity has been initiated, there are preferably provided two ways of stopping the system. In one of these ways, which will typically be the way that a driver will respond on correcting the difficulty which triggered operation of the system, the driver will simply actuate a control, which might be a button worn on the headgear, that will stop the warning/safety activity, and immediately place the system back into a condition monitoring driver head position. The other way of stopping the system, which is the way that will typically be employed by a third party who intervenes, for example, after a stage three level of activity, will be the complete disabling of the system so that it will not continue monitoring driver head position. Such monitoring would only cause a state of confusion inasmuch as this situation will typically arise only when the driver has truly been disabled and cannot return to a normal functioning position. An appropriate signal to indicate to a third party how to effect this kind of system disarming can easily be presented, for example, by an appropriate flashing light, sign or other warning device appropriately placed inside the vehicle. There are many conventional ways in which this latter kind of capability can be enabled, and no specific way forms any part of the present invention.

Circuitry 28, and timer subcircuit 30, can be constructed conventionally either (a) to impose fixed and nonadjustable delay time intervals that define when certain safety and warning actions occur, or (b), and more preferably, to permit user selectability to accommodate normal user/driver-specific behavior regarding one or more of the mentioned, several-stage time intervals. For example, one can, using the system of this invention, choose to allow: (a) a first time interval of about less than one to about three seconds before system implementation of the stage-one interval "warning" activity(ies) action; (b) an additional, annexed, second time interval of about another less than one to about three seconds before system implementation of the second-stage external "warning" activity(ies) action; and (c) a further, annexed, third time interval of about less than one to about three seconds before system implementation of the stage-three, take-control-of-driving-activity(ies) action(s). The exact time employed can, if desired, be anything other than the specific, illustrative intervals just stated. And, as has already been mentioned, these intervals may be completely predetermined, and nonchangeable.

System 24, therefore handily meets an important objective of this invention which is to minimize significantly the occurrence of a sudden catastrophic, and otherwise uncontrollable, accident that results from driver "failure," as indicated by driver head position. The specific way or ways in which system 24 is connected to onboard vehicle systems is a matter of choice. Such connections are preferably entirely conventional in nature. The response produced by system 24 is referred to herein as an emergency response action.

Moving along in this disclosure, as was mentioned earlier, FIGS. 2 and 3 also picture several additional (of many possible) alternative embodiments of the system of the invention, including alternative embodiments of headgear 16 and of monitor structure 18. Thus, on the left side of FIG. 3 is pictured a modification wherein the previously described photo-sensitive film 26, is, in this case, a defined, enclosed field (or monitoring zone) 36 of non-photosensitivity, surrounded by an appropriate field 37 made up of two surrounding, adjacent, ring-like, substantially transparent, photosensitive films 37a, 37b. Zone 36 is sized and positioned like previously-mentioned film 26. Films 37a, 37b are like film 26.

With regard to this modification, each of films 37a, 37b is appropriately connected to a modified form of circuitry 28, which "looks" for the presence of a signal from either film indicating that light from source 17 has struck (is striking) that film. After initial system calibration, and so long as the driver's head is in a normal position, no signal is presented to circuitry 28. Additionally, circuitry 28 has no current "history" of a past-received signal from one of films 37a, 37b.

If the driver's head strays and causes a light-beam impingement to occur initially with film 37a, circuitry 28 notes this, and begins the pattern of staged warning and safety behavior discussed above. This pattern of behavior, in any one of its stages, will be stopped automatically only if light-beam impingement returns to zone 36 (a) directly from film 37a, and (b) only with regard to a yet-unimplemented stage of warning or safety action. The presence of film 37b is provided to guard against an inadvertent miscommunication of "normalcy" which could otherwise occur under circumstances with the point of beam impingement straying outwardly beyond films 37a, 37b, when there would once again be a non-signal condition presented to circuitry 28. In other words, long residence of the point of laser-beam impingement outside of film 37b will not be interpreted as a driver returns to a "normal" head position.

The right side of FIG. 3 shows another alternative form of the invention which is somewhat like the modification just described, and wherein a non-emergency area or zone 60, which is like "areas" 26, 36, is perimetered by, for example, a pair of elongate, thin, inner and outer photosensitive film/conductors, such as those shown generally at 62, 64 in FIG. 3. These conductors which can be small enough in width so that thin transparency or non-transparency is not an issue, effectively "watch" for crossings (impingements) of these two conductors by the light beam from source 17. These conductors cooperate with a suitably modified version of circuitry 28 so that system performance is substantially the same as that just discussed above for the first described system modification.

Looking still further at FIGS. 2 and 3, another modified form of the invention is one wherein headgear 16 carries conventional optical transceiver (light source and receiver) apparatus at the location marked 17 in FIG. 2, and monitor structure 18, wherever located, includes conventional optical retro-reflector material. Preferably, such retro-reflector material is arranged with two retro-reflective elements, such as in the organizations pictured at the left and right sides of FIG. 3. In this modified form of the invention, electrical signals relevant to driver head position are derived from the receiver portion of the transceiver apparatus and conveyed appropriately via a conductor structure like conductor structure 29, which interconnects that receiver portion with circuitry 28.

Various other overall modifications can be made. For example, in one interesting and related modification involving "effective following" of a driver's head orientation as an indication of normal driver alertness, etc., the apparent (or real) open or closed condition of a driver's eyes is something which can also be monitored advantageously to produce warning and safety actions. As an illustration, conventional eye-monitoring systems and technology are available which can readily be linked with the emergency/non-emergency monitoring-zone aspects of the present invention to provide an effective bridge between (a) noting a real change in a driver's head orientation which, from the point of view of the non-emergency monitoring zone "looks like" an eye closure, and (b) noting an actual driver eye-closure condition which is "effectively" the full equivalent of, and thus "looks like", a dangerous change in driver head orientation. Apparatus for "watching" a driver's eyes might, for example, be placed conveniently somewhat near the non-emergency monitoring zones pictured in FIG. 3.

This kind of an "open-eye-condition" modification is certainly contemplated by the present invention.

Thus, an important vehicle warning and safety system, in preferred, several alternative, versions, has been described. The multi-staging and timing capabilities of the system of this invention clearly, and importantly, allow for operation of the system in such a manner that: (1) warnings and safety-control actions occur in a logical script of priority; and (2) warnings and other actions allow for a certain "tolerance" (fixed or selectable) of unusual driver-specific head behavior.

Turning attention for a moment back specifically to FIG. 1, in any one of the several different embodiments for a monitor structure discussed above, and generally pictured in FIG. 3, monitoring can take place in a region, for example, behind the driver's head location, such as is indicated by previously mentioned dash-dot line 20 in FIG. 1. Or, it can take place overhead the driver, as is indicated by dash-double-dot line 22 in FIG. 1. Other locations for monitor structure could of course be chosen if desired. No matter where the monitor structure is positioned, system operation is as has been described above respectively for the several different monitor-structure embodiments which have been discussed and illustrated.

Clearly a further collection of advantages offered by the system of this invention includes: (a) that the proposed system is a relatively inexpensive one; (b) that it is a system which is readily retrofittable in almost (if not completely) all driver-operated vehicles; and (c) that it is not necessarily restrictive in relation to normal driver head movements.

Accordingly, there has been illustrated and described herein a novel safety warning and safety action system which responds to driver head position and orientation as an indication that an out-of-control danger situation may be in existence. And, while a preferred embodiment, and several modifications, of this system invention have been described and illustrated herein, it is appreciated that other variations and modifications are possible and may be made without departing from the spirit of the invention.

I claim:

1. A multistage emergency response and action system usable in a motor vehicle to warn a driver, and if need be outside parties, of an impending driver emergency, and further, to take independent, vehicle-control safety action where necessary, said system comprising light-beam sensing structure installable in a vehicle in a region adjacent the driver seat, defining distributed and differentiated emergency and non-emergency zones generally toward one side of a driver occupying that seat, a driver-wearable head garment including light-beam-active structure having a light-beam source which is directable toward said sensing structure to create a light-beam impingement in relation to the sensing structure, either within said emergency zone or within said non-emergency zone, depending upon the orientation and position of a using driver's head, and response structure operatively interposable (a) at least one of said light-beam-active structure and said sensing structure, and (b) selected, conventional vehicle structure(s), operable, when so interposed, and where a driver is using the system, and is wearing said garment, to initiate a staged and timed series of emergency response actions in relation to selected occurrences of light-beam impingements within said emergency zone.

2. The system of claim 1, wherein said response structure includes timing structure which is responsible for time-staged actions produced by the system.

3. The system of claim 2, wherein said timing structure permits user adjustability of time intervals that are associated with staged system performance.

4. The system of claims 1, 2 or 3, wherein said sensing structure is designed to be borne by the windshield in a vehicle.

5. The system of claims 1, 2 or 3, wherein said non-emergency zone is defined as an enclosed area wherein light-beam impingement is expected normally to occur with the driver's head located and oriented in a manner generally indicative of normal, alert, driver behavior.

6. The system of claim 5, wherein said non-emergency zone is photosensitive, and is capable of producing an electrical output signal in relation to impingement of light from said light-beam source within said zone.

7. The system of claim 5, wherein said non-emergency zone is non-photosensitive.

8. The system of claim 5, wherein there is a boundary extant between said emergency and non-emergency zones, and said boundary is defined by a pair of photosensitive films/conductors.

9. The system of claim 5, wherein said light-beam-active structure takes the form of photo-optical transceiver apparatus including said light-beam source, and said sensing structure includes optical retro-reflector material.

10. A multistage emergency response and action system usable in a motor vehicle to warn a driver, and if need be outside parties, of an impending driver emergency, and further, to take independent, vehicle-control safety action where necessary, said system comprising optical, driver-condition monitoring structure placeable in a vehicle, and effective, when so placed, to define non-emergency and emergency zones in the vehicle and which are relatable to a driver's driving-control capability and noncapability, respectively, said monitoring structure including optical interaction structure for following the apparent, effective orientation and position of a driver's head, with such following taking place on the basis of monitoring a selected category of optical interaction that takes place effectively between a predetermined characteristic of the driver's head and certain optical componentry which forms at least a part of said structure, said interaction structure being disposed external to the driver in the vehicle, and response structure operatively connected to said interaction structure, operatively interposable said interaction structure and selected, conventional vehicle structure (s), and operable, when so interposed, and where a driver is operating the associated vehicle, to initiate a staged and timed series of emergency response actions in relation to selected occurrences of the mentioned selected category of optical interaction between the mentioned predetermined characteristic of the driver's head and said certain optical componentry.

* * * * *